(12) United States Patent
Kim et al.

(10) Patent No.: US 8,747,917 B2
(45) Date of Patent: Jun. 10, 2014

(54) **COMPOSITION COMPRISING *CUDRANIA TRICUSPIDATA* AND *COIX LACHRYMA-JOBI* FOR SUPPRESSING OBESITY OR LOWERING BLOOD SUGAR, AND USE THEREOF**

(75) Inventors: Hyun Ku Kim, Suwon-si (KR); Jeong Ryong Do, Yongin-si (KR); Chan Kyu Han, Yongin-si (KR)

(73) Assignee: Korea Food Research Institute, Seognam-si, Gyeonggi-do (KR)

( * ) Notice: Subject to any disclaimer, the term of this patent is extended or adjusted under 35 U.S.C. 154(b) by 0 days.

(21) Appl. No.: 13/821,644

(22) PCT Filed: Sep. 9, 2011

(86) PCT No.: PCT/KR2011/006694
§ 371 (c)(1),
(2), (4) Date: Mar. 8, 2013

(87) PCT Pub. No.: WO2012/033378
PCT Pub. Date: Mar. 15, 2012

(65) Prior Publication Data
US 2013/0171276 A1    Jul. 4, 2013

(30) Foreign Application Priority Data
Sep. 10, 2010   (KR) ................. 10-2010-0089122

(51) Int. Cl.
*A01N 65/00*   (2009.01)

(52) U.S. Cl.
USPC .......................................... 424/725

(58) Field of Classification Search
None
See application file for complete search history.

(56) References Cited

FOREIGN PATENT DOCUMENTS

| KR | 1019960003738 A | 2/1996 |
|---|---|---|
| KR | 100232671 B1 | 9/1999 |
| KR | 1020010088728 A | 9/2001 |
| KR | 1020050027506 A | 3/2005 |
| KR | 1020050079913 A | 8/2005 |
| KR | 1020050120302 A | 12/2005 |
| KR | 1020060002087 A | 1/2006 |
| KR | 1020070114444 A | 12/2007 |
| KR | 1020050114040 A | 12/2012 |

OTHER PUBLICATIONS

W.Y. Park et al. Hypoglycemic effect of *Cudrania tricuspidata* root bark. Korean J Pharmacogn. 2001, vol. 32, pp. 248-252.
I.K. Kim et al. Effect of the combination of total saponin of red ginseng and Coisis semen for the prevention and treatment of obesity. J. Korean Oriental Med. 2009, vol. 30, pp. 17-25.
J.U. Kim. "Effect of insulin-like action and insulin sensitizing on 3T3-L1 adipocytes from Coicis semen", J. Korean Oriental Med. 2002, vol. 21, pp. 83-91.
S.-I. Cho et al. "Effect of Coicis semen extract on streptozotocin-induced diabetic nephropathy rats", Kor. J. Herbology 2006, vol. 21, pp. 75-81.
J.-Y. Cha et al. "Effect of stem bark extract from *Cudrania tricuspidata* on the concentrations of lipid and lipid peroxidation in rats fed on a cholesterol diet", Korean Journal of Life Science, 2001, vol. 11, No. 4. pp. 328-334.
International Search Report for Application No. PCT/KR2011/006694 dated Apr. 6, 2012.
S.-C. Lim. Effects of Yullmoo (*Coix lachryma-jobi* var. *mayuen stapf.*) ext. on Lipidlowering and Serum Glucose in Hyperlipidemic Rat. Korean J. Plant Res. 2006, vol. 19, pp. 126-129.
B.-S. Ko, et al. A Study on the Hypoglycemic Effects of Crude Extracts of Schizandrae Fructus. J. Korean Soc. Appl. Biol. Chem. 2003, vol. 47, pp. 258-264.
Y. Yoon, et al. Development of Functional Food from Mushroom and Oriental Herbs. 11th World Congress of Food and Science and Technology (Apr. 22-27, 2001). COEX Convention Center, P-14-93, Effects of *Grifola frondosa* on cancer, immunity and side-effect of anticancer drug.
Development of Physiologically Active Food Products from the Leaf and the Fruit of Cudrania triscuspidata. May 29, 2009.
International Preliminary Report on Patentability from PCT/KR2011/006694 issued Mar. 12, 2013.

*Primary Examiner* — Michael Meller
(74) *Attorney, Agent, or Firm* — Lathrop & Gage LLP; Brian C. Trinque (57) ABSTRACT

The present invention relates to a pharmaceutical composition for suppressing obesity or lowering blood sugar which comprises *Cudrania tricuspidata* extract and *Coix lachryma-jobi* extract, and more specifically relates to a pharmaceutical composition for suppressing obesity or lowering blood sugar which comprises *Cudrania tricuspidata* extract and *Coix lachrymajobi* extract, to a functional health food or food additive composition for suppressing obesity or lowering blood sugar which comprises *Cudrania tricuspidata* extract and *Coix lachryma-jobi* extract, to a tablet having an obesity-suppressing function and blood-sugar lowering effect which is produced using *Cudrania tricuspidata* and *Coix lachryma-jobi* as principal raw materials, and to a production method therefor.

4 Claims, 1 Drawing Sheet

COMPOSITION COMPRISING CUDRANIA TRICUSPIDATA AND COIX LACHRYMA-JOBI FOR SUPPRESSING OBESITY OR LOWERING BLOOD SUGAR, AND USE THEREOF

RELATED APPLICATIONS

The present application claims the benefit of priority of International Application No. PCT/KR2011/006694 filed Sep. 9, 2011, which claims priority to Korean Patent Application No. 10-2010-0089122, filed Sep. 10, 2010. The entire contents of each of the above documents are incorporated herein by reference.

TECHNICAL FIELD

The present invention relates to a pharmaceutical composition for suppressing obesity or lowering blood sugar which comprises *Cudrania tricuspidata* extract and *Coix lachryma-jobi* extract. More particularly, the present invention relates to a pharmaceutical composition for suppressing obesity or lowering blood sugar which comprises *Cudrania tricuspidata* extract and *Coix lachryma-jobi* extract, a health functional food or food additive composition for suppressing obesity or lowering blood sugar which comprises *Cudrania tricuspidata* extract and *Coix lachryma-jobi* extract, a tablet having an obesity-suppressing function and a blood sugar-lowering effect which is produced using *Cudrania tricuspidata* and *Coix lachryma-jobi* as principal raw materials, and a preparation method thereof.

BACKGROUND ART

Recent industrialization progress has increased consumption of western-style foods and convenience of facilities has increased the lack of physical activity, weight gain and society's complexity, leading to changes in disease patterns. Unlike in the past, chronic degenerative diseases such as atherosclerosis, hypertension, cancer, obesity and diabetes have become the leading cause of death. Of these chronic degenerative diseases, especially diabetes, together with obesity, has become a growing concern, because the number of patients has rapidly increased and the age-at-onset of diabetes has become younger.

Diabetes is a disease characterized by the excretion of blood glucose into the urine, and is one of chronic degenerative diseases substantially incurable. Alterations in eating habits due to rapid industrialization progress have prolonged the life expectancy, but have been implicated in the rising prevalence of chronic degenerative diseases such as diabetes or the like. The prevalence of diabetes in Korea is reported to reach approximately 5-10%, and tends to steadily increase. Diabetes is certain to be a serious national health problem in the 21st century. Diabetes is also a global public health crisis, and the third most prevalent disease in the world. Diabetes causes complications in many organs such as the retina, kidney, nerve, and cardiovascular system, and thus continues to be a particularly serious social problem.

Because obesity is a cause of hypertension, diabetes, cardiovascular diseases, and various cancers, and the medical care costs of obesity-related diseases are increasing, investigation of materials having a body fat-reducing effect and demonstration of the effect thereof become a major concern worldwide. Many studies for treating and preventing obesity have been also actively conducted in many countries. Present methods include a diet therapy decreasing food-intake to reduce energy, an exercise therapy increasing energy consumption, surgical therapies such as cutting off parts of inner organs or suction of fat, and drug therapies using a metabolic accelerator, an appetite-suppressant or a digest/absorption-suppressant.

However, no satisfactory method has been reported and the above methods have side effects such as yo-yo effect that obesity becomes more serious after stopping the therapy; unbalanced nutrition condition due to diet therapy; or infections due to decreased immunity. In particular, the drug therapy causes depression, insomnia, indigestion, or the like. Therefore, it is strongly desired to develop a safe and effective method for accelerating body weight loss other than the conventional methods.

*Cudrania tricuspidata* ((Carr.) Bureau ex Lavallee) is a deciduous tree belonging to the family Moraceae, and is also called *Cudrania*, Silkworm Thorn, and Chinese Mulberry. *Cudrania tricuspidata* contains a variety of active ingredients in the root bark, xylem, stem bark, and leaves. Traditionally, the root barks, stems, leaves, stem barks, and fruits of *Cudrania tricuspidata* have been used in traditional medicines as an antihypertensive, an antitubercular agent, an antifebrile, an antitussive, an expectorant, a diuretic, an antihemorrhagic, and an anti-apoplexy drug, and also used for athlete's foot as an antifungal drug, and for chronic dyspepsia caused by weak digestive systems.

The fruit of *Cudrania tricuspidata* is a spherical aggregate fruit, and about 2.5 cm in diameter. It ripens to red color in September to October, and the flesh is sweet and edible. Reportedly, the fruit contains useful organic compounds such as vitamin B, B1, B2, C, linolenic acid, glucose, maltose, fructose, malic acid, citric acid, etc., and the stem bark contains a large amount of ingredients effective for lung cancer, colon cancer, skin cancer, and cervix cancer. *Cudrania tricuspidata* contains flavonoids that are known to have anti-cancer effects, and thus its medicinal uses were reported in traditional medicine books such as DonguiBogam, yaksunggam, and Bonchokangmok Meanwhile, recent studies have been continuously conducted on the use of *Cudrania tricuspidata* extracts. There are Korean patents regarding *Cudrania tricuspidata*, including a *Cudrania tricuspidata* drink and a preparation method thereof, a method for manufacturing *Cudrania tricuspidata* granules using sorbitol, functional rice coated with the root extract of *Cudrania tricuspidata* and a preparation method thereof, etc., but there is no report of the inhibitory effects of *Cudrania tricuspidata* extract on obesity and diabetes as disclosed in the present invention.

*Coix lachryma-jobi* (Coicis semen) has the efficacies of invigorating the spleen to eliminate dampness, removing obstruction to stop diarrhea, and clearing up heat and promoting pus discharge, and contains starch, fatty oil, Coixol, sterol, amino acid, vitamin B1, Coixenolide as main ingredients. *Coix lachryma-jobi* is an annual grass crop belonging to the family Poaceae, and also called adlay, *Coix* seeds, pearl barley, Job's tears, and semen coicis. It has anti-inflammatory and anti-carcinogenic activities, and cholesterol-lowering, sedative and analgesic effects, and thus used as an injectable formulation for neuralgia or arthralgia. *Coix lachryma-jobi* is also useful for dyspepsia, arthralgia, and muscle cramps and effective for recovery of fatigue and for the prevention of melasma and freckle to remove facial blemishes. It has an excellent whitening effect, and an effect of expanding and contracting peripheral nerves, and thus is useful for acne, edema, beriberi and neuralgia.

However, there are no reports or descriptions that the mixture of *Cudrania tricuspidata* and *Coix lachryma-jobi* extracts is able to suppress obesity and diabetes at the same time.

The present inventors have made many efforts to find a natural substance capable of suppressing obesity and diabetes at the same time. They found that the *Cudrania tricuspidata* and *Coix lachryma-jobi* extracts have excellent inhibitory activities on ATP citrate lyase and $H_2O_2$-induced apoptosis of pancreatic islets so as to suppress obesity and diabetes, thereby completing the present invention.

DISCLOSURE

Technical Problem

An object of the present invention is to provide a pharmaceutical composition for suppressing obesity or lowering blood sugar, which comprises *Cudrania tricuspidata* extract and *Coix lachryma-jobi* extract.

Another object of the present invention is to provide a health functional food or food additive composition for suppressing obesity or lowering blood sugar, which comprises *Cudrania tricuspidata* extract and *Coix lachryma-jobi* extract.

Still another object of the present invention is to provide a *Cudrania tricuspidata* and *Coix lachryma-jobi* tablet having an obesity-suppressing or blood sugar-lowering effect, which comprises *Cudrania tricuspidata* extract and *Coix lachryma-jobi* extract.

Still another object of the present invention is to provide a method for preparing a *Cudrania tricuspidata* and *Coix lachryma-jobi* tablet, comprising the steps of mixing *Cudrania tricuspidata* and *Coix lachryma-jobi* with one or more herbal medicines selected from the group consisting of red ginseng, ginseng, *Dioscorea* Rhizome, the leaf of *Morus alba*, the fruit, stem, and leaf of *Hovenia dulcis*, *Glycyrrhiza uralensis*, cinnamon bark, Golden thread, *Rubus coreanus* Miquel, Dodder seed, *Cnidium* fruit, *Lycium* fruit, *Schizandra* fruit and *Astragalus* root so as to prepare a mixture; adding one or more functional substances selected from the group consisting of vitamins, saccharide, squalene, taurine, herb, octacosanol and sodium alginate to the mixture and mixing them so as to prepare a mixture of *Cudrania tricuspidata*, *Coix lachryma-jobi*, herbal medicines, and functional substances; ripening the mixture at 5~20° C. for 10~20 hours; preparing tablets using a tabletting machine; and coating the tablets with a hydroxypropyl methylcellulose solution.

TECHNICAL SOLUTION

Figure 1:
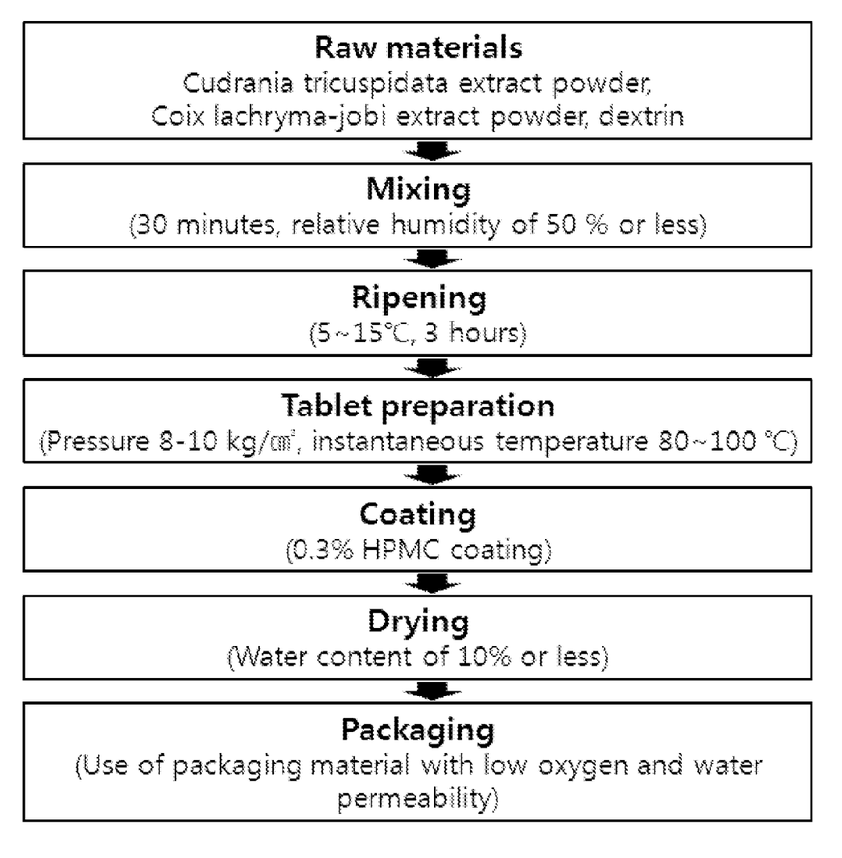
FIG. 1 is a production flow chart of *Cudrania tricuspidata* and *Coix lachryma-jobi* tablet of the present invention.

In one aspect to achieve the above objects, the present invention provides a pharmaceutical composition for suppressing obesity or lowering blood sugar, which comprises *Cudrania tricuspidata* extract and *Coix lachryma-jobi* extract.

As used herein, the term "*Cudrania tricuspidata*" is a deciduous tree belonging to the family Moraceae, and is also called *Cudrania*, Silkworm Thorn, and Chinese Mulberry. *Cudrania tricuspidata* contains a variety of active ingredients in the root bark, xylem, stem bark, and leaves. Traditionally, the root barks, stems, leaves, stem barks, and fruits of *Cudrania tricuspidata* have been used in traditional medicines as an antihypertensive, an antitubercular agent, an antifebrile, an antitussive, an expectorant, a diuretic, an antihemorrhagic, and an anti-apoplexy drug, and also used for athlete's foot as an antifungal drug, and for chronic dyspepsia caused by weak digestive systems. In the present invention, anti-obesity and anti-diabetic effects of *Cudrania tricuspidata* were investigated for the first time. According to embodiments of the present invention, it was found that the *Cudrania tricuspidata* extract has anti-obesity and anti-diabetic effects (Tables 1 and 2), and a blood sugar-lowering effect (Table 5). Further, the *Cudrania tricuspidata* extract was found to suppress lipid accumulation upon adipocyte differentiation (Table 6).

As used herein, the term "*Coix lachryma-jobi*" is an annual grass crop belonging to the family Poaceae, and also called adlay, *Coix* seeds, pearl barley, Job's tears, and semen coicis. Reportedly, it has anti-inflammatory and anti-carcinogenic activities. In the present invention, it was found that the *Coix lachryma-jobi* extract has anti-obesity and anti-diabetic effects (Tables 1 and 2), and a blood sugar-lowering effect (Table 5). Further, the *Cudrania tricuspidata* extract was found to suppress lipid accumulation upon adipocyte differentiation).

Moreover according to embodiments of the present invention, an equivalent mixture of the *Cudrania tricuspidata* and *Coix lachryma-jobi* extracts showed more excellent anti-obesity and anti-diabetic effects than the *Cudrania tricuspidata* extract and the *Coix lachryma-jobi* extract alone (Tables 1 and 2), which supports that the mixed extract of the present invention has an obesity-suppressing or blood sugar-lowering effect, and more preferably, both of the obesity-suppressing and blood sugar-lowering effects.

The present invention is characterized in that the *Cudrania tricuspidata* extract and the *Coix lachryma-jobi* extract are used as active ingredients. Specifically, each of the *Cudrania tricuspidata* extract and the *Coix lachryma-jobi* extract is prepared, and then they are mixed at a proper ratio so as to prepare the mixed extract. A weight ratio of the *Cudrania tricuspidata* extract and the *Coix lachryma-jobi* extract may be preferably 1:1.

The *Cudrania tricuspidata* extract and the *Coix lachryma-jobi* extract of the present invention may be, but is not limited to, any one of a liquid extract obtained by extraction, a diluted or concentrated liquid extract, a dry product obtained by drying the liquid extract, a crude purified product thereof, and a purified product thereof. In addition, they may be each independently extracted using an extraction solvent typically used in the art, and preferably extracted using water, alcohol having 1 to 6 carbons or a mixture thereof. More preferably, the alcohol may be ethanol, methanol, or butanol, and much more preferably, an ethanol aqueous solution may be used for extraction.

Preferably, the pharmaceutical composition comprising *Cudrania tricuspidata* and *Coix lachryma-jobi* of the present invention can be used for prevention or treatment of obesity and diabetes through reduction of blood-sugar level.

When inhibitory activities on ATP citrate lyase and $H_2O_2$-induced apoptosis of pancreatic islets were examined, the *Cudrania tricuspidata* and *Coix lachryma-jobi* extracts according to the present invention showed excellent inhibitory activities on ATP citrate lyase and $H_2O_2$-induced apoptosis of pancreatic islets, indicating obesity-suppressing and blood sugar-lowering effects (Table 2). Water and ethanol extracts of *Cudrania tricuspidata* and *Coix lachryma-jobi* showed lower glycemic index than the control group glucose, indicating that each of the *Cudrania tricuspidata* and *Coix lachryma-jobi* extracts has excellent blood sugar-lowering effect (Table 5).

The *Cudrania tricuspidata* and *Coix lachryma-jobi* extracts of the present invention may further comprise a pharmaceutically acceptable carrier. For formulation, any one or more selected from a filler, an extender, a binder, a wetting agent, a disintegrant, a surfactant, and a lubricant commonly used may be used, and they may be included in an amount of 0.1-5 parts by weight, based on 100 parts by weight of *Cudrania tricuspidata* extract and *Coix lachryma-jobi* extract.

Specifically, when they are formulated in a form of tablet or capsule, any one or more excipients selected from lactose, starch, cellulose, and microcrystalline cellulose; any one or more binders selected from starch, dextrin, honey, syrup, and cellulose; any one or more disintegrants selected from crystalline cellulose, starch, calcium carboxymethyl cellulose, and methylcellulose; and any one or more lubricants selected from magnesium stearate, glyceryl behenate, talc, and hydrogenated vegetable oil may be used.

In the present invention, the *Cudrania tricuspidata* and *Coix lachryma-jobi* extracts may be administered in a typical manner via oral, rectal, intravenous, intraarterial, intraperitoneal, intramuscular, intrasternal, transdermal, topical, intraocular or intracutaneous route. Once administration dosage for adults is 0.1 to 10 g, and preferably 0.5 to 5 g, and the level of the administration dosage may appropriately vary depending on a patient's gender, age, health conditions, and diet, administration time, administration method, the kind of drugs used in combination, and disease severity. The administration may be performed once or several times a day. Therefore, the scope of the present invention is not limited to the administration dosage in all aspects. The mixture of *Cudrania tricuspidata* and *Coix lachryma-jobi* extracts of the present invention has been traditionally used as a food and medicine, and thus there is no particular limitation in its administration dosage. The pharmaceutical composition comprising the *Cudrania tricuspidata* and *Coix lachryma-jobi* extracts of the present invention should be prepared considering its effective range, and administration of a unit dosage formulation prepared thereby can be monitored, if necessary. Further, a specialized administration method may be used according to the expert's decision and patient's request or it may be administered several times at regular intervals.

In another aspect, the *Cudrania tricuspidata* and *Coix lachryma-jobi* extracts of the present invention may be used as a health functional food or food additive composition for the prevention or treatment of obesity and diabetes.

The *Cudrania tricuspidata* and *Coix lachryma-jobi* extracts of the present invention may be used in a variety of foods and drinks for the improvement of obesity and diabetes. The type of foods comprising the *Cudrania tricuspidata* and *Coix lachryma-jobi* extracts of the present invention is not particularly limited, and is exemplified by meats, sausages, breads, chocolates, candies, snacks, cookies, pizza, instant noodles, other noodles, gums, dairy products including ice creams, various soups, beverages, teas, drinks, alcoholic beverages and vitamin complexes. Normally, the extract may be added to such food or drink in an amount of 0.01 to 10 parts by weight, preferably 0.05 to 1 part by weight. However in the case of long-term intake for the purpose of health and hygiene improvement or health control, a smaller amount may be used.

The food composition of the present invention may further comprise additional ingredients such as a variety of proteins, fats, nutrients, seasoning, flavors, or natural carbohydrates, as in the conventional drinks. The carbohydrate may be exemplified by conventional sugars, such as monosaccharide (e.g., glucose, fructose, etc.), disaccharide (e.g., maltose, sucrose, oligosaccharide, etc.), and polysaccharide (e.g., dextrin, cyclodextrin, etc.), and sugar alcohols such as xylitol, sorbitol, erythritol, etc. As the flavor, a natural flavor (e.g., thaumatin, a stevia extract such as rebaudioside A and glycyrrhizin) and a synthetic flavor (e.g., saccharine, aspartame, etc.) may be used.

In addition to the above ingredients, the composition of the present invention may comprise various nutrients, vitamins, electrolytes, a flavor, a coloring agent, pectic acid and a salt thereof, alginic acid and a salt thereof, an organic acid, a protective colloid thickener, a PH adjuster, a stabilizer, a preservative, glycerin, alcohol, a carbonating agent used for a carbonated drink, etc. Also, the composition of the present invention may comprise flesh for the preparation of natural fruit juice, fruit juice drinks, and vegetable drinks. Each of such ingredients may be used independently or in any combination thereof. Although the percentages of such additives are not important, the additives are generally selected in the range of 0.01 to 0.1 parts by weight, based on 100 parts by weight of the composition of the present invention.

In still another aspect, the present invention provides a *Cudrania tricuspidata* and *Coix lachryma-jobi* tablet for suppressing obesity or lowering blood sugar, which comprises *Cudrania tricuspidata* extract and *Coix lachryma-jobi* extract. Preferably, the tablet of the present invention provides obesity-suppressing and blood sugar-lowering effects at the same time.

Preferably, the tablet may comprise any one or more herbal medicines selected from the group consisting of red ginseng, ginseng, *Dioscorea* Rhizome, the leaf of *Morus alba*, the fruit, stem, and leaf of *Hovenia dulcis, Glycyrrhiza uralensis*, cinnamon bark, Golden thread, *Rubus coreanus* Miquel, Dodder seed, *Cnidium* fruit, *Lycium* fruit, *Schizandra* fruit and *Astragalus* root.

The *Cudrania tricuspidata* and *Coix lachryma-jobi* tablet of the present invention and *Cudrania tricuspidata* and *Coix lachryma-jobi* used as main ingredients for the preparation of the *Cudrania tricuspidata* and *Coix lachryma-jobi* tablet may be those obtained by processing any one or more selected from the leaf, stem, and fruit in the form of powder. They may be processed in the form of powder by any method known in the art without limitation, and for example, they may be pulverized in the form of powder using a pulverizer. After pulverization by a pulverizer, they may be further pulverized by passing them through a mesh. Preferably, the powder pulverized by 40~100 mesh may be used.

The *Cudrania tricuspidata* and *Coix lachryma-jobi* tablet of the present invention and *Cudrania tricuspidata* and *Coix lachryma-jobi* used as main ingredients for the preparation of the *Cudrania tricuspidata* and *Coix lachryma-jobi* tablet may be those obtained by extracting any one or more selected from the leaf, stem, and fruit in a solvent, filtering and spray-drying the obtained *Cudrania tricuspidata* and *Coix lachryma-jobi* extract to obtain a solid phase of *Cudrania tricuspidata* and *Coix lachryma-jobi*, and then processing the solid in the form of powder. They may be processed in the form of powder by any method known in the art without limitation, and for example, they may be pulverized in the form of powder using a pulverizer. After pulverization, they may be further pulverized by passing them through a mesh. The powder pulverized by preferably 10~100 mesh, and more preferably 40~100 mesh may be used.

Hereinafter, the *Cudrania tricuspidata* and *Coix lachryma-jobi* tablet of the present invention and *Cudrania tricuspidata* and *Coix lachryma-jobi* used for the preparation of the *Cudrania tricuspidata* and *Coix lachryma-jobi* tablet are defined as *Cudrania tricuspidata* and *Coix lachryma-jobi* powders.

Further, the *Cudrania tricuspidata* and *Coix lachryma-jobi* may be cut in a predetermined size of 1~20 mm, preferably 1~15 mm, more preferably 1~10 mm, and much more preferably 1~5 mm.

In the present invention, the *Cudrania tricuspidata* and *Coix lachryma-jobi* may be extracted by using purified water or ethanol as the solvent. The ethanol may be preferably 50% to 100% ethanol, and more preferably 70% ethanol. If purified water is used as the solvent, *Cudrania tricuspidata* and *Coix lachryma-jobi* are added to 3~50-fold of purified water, preferably 3~30 fold of purified water, based on the weight of *Cudrania tricuspidata* and *Coix lachryma-jobi*, and then extracted at 90~110° C. until the content of purified water reaches 10~50%, thereby obtaining the *Cudrania tricuspidata* and *Coix lachryma-jobi* extract. If ethanol is used as the solvent, *Cudrania tricuspidata* and *Coix lachryma-jobi* are added to 3~50-fold of ethanol, preferably 3~10 fold of ethanol, based on the weight of *Cudrania tricuspidata* and *Coix lachryma-jobi*, and then extracted at 50~60° C. for 1~5 hours, thereby obtaining the *Cudrania tricuspidata* and *Coix lachryma-jobi* extract.

The *Cudrania tricuspidata* and *Coix lachryma-jobi* extract may be obtained by extraction in the presence of microwave with a wavelength of 1 mm~1 m in the solvent at 50~60° C. for 1~2 hours, and the solvent may be the above mentioned purified water or ethanol.

A minor ingredient used for the preparation of the *Cudrania tricuspidata* and *Coix lachryma-jobi* tablet of the present invention may be one or more herbal medicines selected from the group consisting of red ginseng, ginseng, *Dioscorea* Rhizome, the leaf of *Morus alba*, the fruit, stem, and leaf of *Hovenia dulcis*, *Glycyrrhiza uralensis*, cinnamon bark, Golden thread, *Rubus coreanus* Miquel, Dodder seed, *Cnidium* fruit, *Lycium* fruit, *Schizandra* fruit, *Astragalus* root, Atractylodes Rhizome white, *Poria* Sclerotium, Rehmannia root, Paeoniae Radix, *Cnidium* Rhizome, Korean angelica and *Cassia* bark, and preferably two or more thereof. According to the specific embodiment of the present invention, two herbal medicines were included to prepare the tablet.

The herbal medicine used as the minor ingredient for the preparation of the *Cudrania tricuspidata* and *Coix lachryma-jobi* tablet of the present invention may be in the form of powder, and the pulverization process of the herbal medicines may be performed in the same manner as in the above mentioned pulverization process of *Cudrania tricuspidata* and *Coix lachryma-jobi*.

Upon the preparation of the *Cudrania tricuspidata* and *Coix lachryma-jobi* tablet of the present invention, the herbal medicine may be comprised in an amount of 10~50 parts by weight, based on 100 parts by weight of *Cudrania tricuspidata* extract and *Coix lachryma-jobi* extract. Upon the preparation of the *Cudrania tricuspidata* and *Coix lachryma-jobi* tablet of the present invention, if the herbal medicine is used in an amount of less than 10 parts by weight, based on 100 parts by weight of *Cudrania tricuspidata* extract and *Coix lachryma-jobi* extract, the herbal medicine functions weakly, and if the herbal medicine is used in an amount of more than 50 parts by weight, based on 100 parts by weight of *Cudrania tricuspidata* extract and *Coix lachryma-jobi* extract, the increased content of herbal medicine does not greatly contribute to functional improvement of the herbal medicine. Therefore, it is preferable that the herbal medicine is included in an amount of 10~50 parts by weight, based on 100 parts by weight of *Cudrania tricuspidata* extract and *Coix lachryma-jobi* extract, upon the preparation of the *Cudrania tricuspidata* and *Coix lachryma-jobi* tablet of the present invention.

In order to improve the functions of the *Cudrania tricuspidata* and *Coix lachryma-jobi* tablet, the present invention may further comprise any one or more functional ingredients, preferably two or more functional ingredients selected from the group consisting of vitamin, saccharide, squalene, taurine, herb, octacosanol, and sodium alginate, in addition to *Cudrania tricuspidata*, *Coix lachryma-jobi*, and the herbal medicines. According to the specific embodiment of the present invention, two or more functional ingredients were included to prepare the tablet.

Vitamin may be used as the functional ingredient. At this time, vitamin may be used in an amount of 1~5 parts by weight, based on 100 parts by weight of *Cudrania tricuspidata* extract and *Coix lachryma-jobi* extract. The vitamin may be any one or more selected from vitamin D, vitamin B1, vitamin B2, vitamin B6, vitamin B12, vitamin B13, vitamin C, biotin, folic acid, choline, inositol, vitamin L, and vitamin P.

Saccharide may be used as the functional ingredient. At this time, saccharide may be used in an amount of 1~10 parts by weight, based on 100 parts by weight of *Cudrania tricuspidata* extract and *Coix lachryma-jobi* extract. The saccharide may be any one or more selected from lactose, oligosaccharide, sugar, fructose, glucose, dextrin, xylitol, erythritol, palatinose, mannitol, maltitol, inositol, and quercitol.

Herb may be used as the functional ingredient. At this time, herb may be used in an amount of 1~10 parts by weight, based on 100 parts by weight of *Cudrania tricuspidata* extract and *Coix lachryma-jobi* extract. The herb may be any one or more selected from green tea, gulfweed, aloe, mugwort, *chlorella*, black tea, oolong tea, *Akebia quinata*, *Aralia elata*, and *Ulmus davidiana*.

Sodium alginate may be used as the functional ingredient. At this time, sodium alginate may be used in an amount of 1~5 parts by weight, based on 100 parts by weight of *Cudrania tricuspidata* extract and *Coix lachryma-jobi* extract.

Two or more functional ingredients selected from vitamin, saccharide, squalene, taurine, herb, octacosanol, and sodium alginate may be used in each content ratio.

Also, in order to improve the functions of the *Cudrania tricuspidata* and *Coix lachryma-jobi* tablet, the present invention may further comprise Fenugreek seed powder or ramie leaf powder as a secondary functional ingredient.

The secondary functional ingredient, Fenugreek seed powder or ramie leaf powder may be used in an amount of 0.5~10 parts by weight, based on 100 parts by weight of *Cudrania tricuspidata* extract and *Coix lachryma-jobi* extract. Also, the secondary functional ingredient may be added to 3~30 fold of purified water, based on the weight of the secondary functional ingredient, and extracted at 90~110° C. until the content of purified water reaches 5~50%, preferably 5~35%, more preferably 5~30%, and much more preferably 5~25%, and then filtered and pulverized by spray-drying to control the particle size within the range of 10~100 mesh.

In still another aspect, the present invention provides a method for preparing a *Cudrania tricuspidata* and *Coix lachryma-jobi* tablet, comprising the steps of (a) mixing *Cudrania tricuspidata* and *Coix lachryma-jobi* with 10~50 parts by weight of one or more herbal medicines selected from the group consisting of red ginseng, ginseng, *Dioscorea* Rhizome, the leaf of *Morus alba*, the fruit, stem, and leaf of *Hovenia dulcis*, *Glycyrrhiza uralensis*, cinnamon bark, Golden thread, *Rubus coreanus* Miquel, Dodder seed, *Cnidium* fruit, *Lycium* fruit, *Schizandra* fruit and *Astragalus* root, based on 100 parts by weight of *Cudrania tricuspidata* extract and *Coix lachryma-jobi* extract so as to prepare a mixture; (b) adding to the mixture one or more functional substances selected from the group consisting of 1~5 parts by weight of vitamin, 1~10 parts by weight of saccharide, 0.5~5 parts by weight of squalene, 0.5~5 parts by weight of taurine, 1~10 parts by weight of herb, 0.1~5 parts by weight of octacosanol and 1~5 parts by weight of sodium alginate, based on 100 parts by weight of *Cudrania tricuspidata* extract and *Coix lachryma-jobi* extract, and mixing them so as to prepare a mixture of *Cudrania tricuspidata, Coix lachryma-jobi*, herbal medicines, and functional substances; (c) ripening the mixture at 5~20° C. for 10~20 hours; (d) preparing tablets using a tabletting machine; and (e) coating the tablets with a hydroxypropyl methylcellulose solution.

Upon the preparation of the *Cudrania tricuspidata* and *Coix lachryma-jobi* tablet of the present invention, mixing of the ingredients for *Cudrania tricuspidata* and *Coix lachryma-jobi* tablet may be performed at 10~20° C. for 20~60 minutes in order to mix the ingredients uniformly. In this regard, when the ingredients for *Cudrania tricuspidata* and *Coix lachryma-jobi* tablet are mixed, *Cudrania tricuspidata* and *Coix lachryma-jobi* and herbal medicines may be mixed at once, and when the functional substances are further added, the *Cudrania tricuspidata* and *Coix lachryma-jobi*, herbal medicines and functional substances may be mixed at once, or herbal medicines and functional substances may be mixed primarily, and then *Cudrania tricuspidata* and *Coix lachryma-jobi* may be added secondarily.

Upon the preparation of the *Cudrania tricuspidata* and *Coix lachryma-jobi* tablet of the present invention, the ingredients for *Cudrania tricuspidata* and *Coix lachryma-jobi* tablet may be ripened at 10~30° C. for 1~5 hours, preferably 10~20° C. for 2~4 hours, and more preferably at 20° C. for 3 hours, after they are mixed. The ingredients of the *Cudrania tricuspidata* and *Coix lachryma-jobi* tablet have different water contents. Thus, it is preferable that the ingredients of the *Cudrania tricuspidata* and *Coix lachryma-jobi* tablet are mixed and then aged, in order to maintain water balance between the ingredients of the *Cudrania tricuspidata* and *Coix lachryma-jobi* tablet for effective preparation of the *Cudrania tricuspidata* and *Coix lachryma-jobi* tablet.

Upon the preparation of the *Cudrania tricuspidata* and *Coix lachryma-jobi* tablet of the present invention, the *Cudrania tricuspidata* and *Coix lachryma-jobi* tablet may comprise any one or more selected from an excipient, a binder, a disintegrant, and a lubricant.

Upon the preparation of the *Cudrania tricuspidata* and *Coix lachryma-jobi* tablet of the present invention, the *Cudrania tricuspidata* and *Coix lachryma-jobi* tablet may comprise any one or more selected from an excipient, a binder, a disintegrant, and a lubricant in an amount of 0.1~5 parts by weight, based on 100 parts by weight of *Cudrania tricuspidata* extract and *Coix lachryma-jobi* extract.

The excipient may be any one or more selected from lactose, starch, cellulose, and microcrystalline cellulose.

The binder may be any one or more selected from starch, dextrin, honey, syrup, and cellulose.

The disintegrant may be any one or more selected from crystalline cellulose, starch, calcium carboxymethyl cellulose, and methylcellulose.

The lubricant may be any one or more selected from magnesium stearate, glyceryl behenate, talc, and hydrogenated vegetable oil.

The above mentioned excipient, binder, disintegrant, and lubricant are ingredients commonly used for the preparation of tablets. Thus, if these ingredients are used in the present invention, they may be properly selected and used by those skilled in the art.

Upon the preparation of the *Cudrania tricuspidata* and *Coix lachryma-jobi* tablet of the present invention, the *Cudrania tricuspidata* and *Coix lachryma-jobi* tablet is prepared using a tabletting machine, and then the surface of the *Cudrania tricuspidata* and *Coix lachryma-jobi* tablet is coated so as to prepare a surface-coated *Cudrania tricuspidata* and *Coix lachryma-jobi* tablet. The coating agent applied to the surface of the tablet may be any coating agent, as long as it is not harmful to human and is used as a coating agent in food-related fields. For example, hydroxypropyl methylcellulose (HPMC), Shellac, gelatin, Arabic Gum, cacao, or lecitin may be used to coat the surface of the tablet, and more preferably, a 0.3% hydroxypropyl methylcellulose solution may be used.

When the surface of the *Cudrania tricuspidata* and *Coix lachryma-jobi* tablet is coated with the coating agent, the coating agent may be applied to the surface of the *Cudrania tricuspidata* and *Coix lachryma-jobi* tablet using a spray system. Meanwhile, the method of coating the surface of *Cudrania tricuspidata* and *Coix lachryma-jobi* tablet with the coating agent may be properly selected and used by those skilled in the art.

In still another embodiment, the present invention provides a method for treating obesity or diabetes, comprising the step of administering the pharmaceutical composition to patient with obesity or diabetes.

In the present invention, the patient with obesity or diabetes means all mammals including human with obesity or diabetes or at the risk of obesity or diabetes. The patient can be effectively treated by administering the pharmaceutical composition comprising the *Cudrania tricuspidata* and *Coix lachryma-jobi* extracts of the present invention to the patient with obesity or diabetes.

As used herein, the term "administration" means introduction of the pharmaceutical composition of the present invention into a patient with obesity or diabetes by any proper method, and the pharmaceutical composition may be administered via the oral or parenteral route, as long as it is able to reach the desired tissue.

The therapeutic method of the present invention may comprise the step of administering the pharmaceutical composition comprising the *Cudrania tricuspidata* and *Coix lachryma-jobi* extracts at a pharmaceutically effective amount. The total daily dose should be determined through appropriate medical judgment by a physician, and administered once or several times. With respect to the objects of the present invention, the specific therapeutically effective dose level for any particular patient may vary depending on various factors well known in the medical art, including the kind and degree of the response to be achieved, concrete compositions according to whether other agents are used therewith or not, the patient's age, body weight, health conditions, gender, and diet, the time and route of administration, the secretion rate of the composition, the time period of therapy, other drugs used in combination or coincidentally with the specific composition, and like factors well known in the medical arts.

BEST MODE

Hereinafter, the present invention will be described in detail with reference to Examples and Experimental Examples. However, these Examples and Experimental Examples are for illustrative purposes only, and the invention is not intended to be limited by these Examples and Experimental Examples.

Example 1

Selection of Natural Products with Anti-Obesity and Anti-Diabetic Activities Based on the data in herbology, Dongui Bogam or the like, 60 kinds of natural products commonly used in the prescription of obesity and diabetes and allowable as food were examined. Among them, 15 kinds of natural products showing inhibitory activities on ATP citrate lyase (anti-obesity) and $H_2O_2$-induced oxidative damage of pancreatic islets (anti-diabetes) were selected and examined.

*Perilla frutescens*, *Benincasa hispida*, Golden thread, *Akebia quinata*, ripened pumpkin, Phyllostachydis Folium, Chinese wolfberry root bark, *Angelica pubescentis*, *Ramulus mori*, *Cornus officinalis*, *Schizandra* fruit, *Astragalus* root, *Coix lachryma-jobi*, *Cudrania tricuspidata*, and broccoli used as samples in this experiment were purchased at Kyungdong market. All herbal medicines were dried by hot air drying at 45° C., and the dried samples were pulverized using a pulverizer (M20, IKA, Germany), and then sealed in a 0.2 mm PE film, followed by storage in a freezer before use.

Example 2

Assessment of Inhibitory Effect on ATP-Citrate Lyase (Anti-Obesity Effect)

In order to examine inhibitory effects of 15 kinds of natural products selected in Example 1 on ATP-citrate lyase activity (anti-obesity), the following experiment was performed.

12-week-old Sprague-Dawley male rats were fed with high carbohydrate diet (63% sucrose, 30% casein, 4% salt mixture, 2% cellulose powder, 1% vitamin mixture, and 0.1% choline chloride) for 3 days. After 3 days, the male rats were sacrificed by cervical dislocation. The liver was excised and homogenized in ice-cold buffer (0.25 M sucrose, 50 mM Tris-HCl, pH 8.2, 10 mM $MgCl_2$, 5 mM DTT (dithiothreitol) and 0.1 mM PMSF (phenylmethylsulfonyl fluoride)). Next, the homogenate was precipitated with 40% saturated ammonium sulfate solution, and centrifuged at 4° C. and 17,500×g for 15 minutes. The supernatant was filtered and high-speed centrifuged (at 4° C. and 100,000×g for 1 hour), followed by fractionation. The resulting fraction was stored at −80° C. and used as an ATP-citrate lyase sample. ATP citrate lyase activity of the liver of the male rat was measured by malate dehydrogenase-catalyzed reduction of oxaloacetate by NADH.

Example 3

Assessment of Inhibitory Effect on Oxidative Damage of Pancreatic Islets (Anti-Diabetic Effect)

In order to examine inhibitory effects of 15 kinds of natural products selected in Example 1 on oxidative damage of pancreatic islets (anti-diabetes), the following experiment was performed.

The pancreas was excised from the rat, and treated with a collagenase V solution (2 mg/ml) at 37° C. for 15 minutes, and digestion was stopped by adding cold Krebs-ringer bicarbonate buffer. After washing three times with the same buffer, islets were handpicked under a stereomicroscope. The cells were cultured in RPMI 1640 supplemented with 10% fetal calf serum, 100 U/ml penicillin and 100/ml streptomycin at 37° C., 95% $O_2$ and 5% $CO_2$ for 24 hours. Pancreatic islets were transferred to 96 well plates at a density of 10 islets/well in 150 μl RPMI1640 medium and pre-incubated overnight. After pre-incubation, the natural product samples prepared in Example 1 were added to each well, and incubated at 37° C. for 48 hours. Then, 500 μM $H_2O_2$ was added to each well, and incubated for 2 hours. 10 μl of MTT solution was added thereto, and further incubated at 37° C. for 4 hours. The supernatant was discarded, and 100 μl of DMSO (dimethylsulphoxide) was added into each well to dissolve the dark blue crystal formazan. The absorbance was determined at 570 nm to analyze the inhibitory effects on oxidative damage of pancreatic islets.

Based on the results of Examples 2 and 3, 15 kinds of natural products showing excellent inhibitory activities on ATP citrate lyase and $H_2O_2$-induced oxidative damage of pancreatic islets were selected from 60 kinds of natural products, and their $IC_{50}$ values were shown in the following Table 1.

TABLE 1

| Group | ATP citrate lyase (anti-obesity) | Apoptosis of islets (anti-diabetes) |
|---|---|---|
| H1 (*Perilla frutescens*) | 2.36 ± 2.4$^b$ | 61.2 ± 3.5$^e$ |
| H2 (*Benincasa hispida*) | 10.6 ± 1.5$^a$ | 60.9 ± 4.2$^e$ |
| H3 (Golden thread) | 37.4 ± 2.4$^{cd}$ | 57.3 ± 4.3$^{de}$ |
| H4 (*Akebia quinata*) | 40.7 ± 3.4$^{cd}$ | 55.9 ± 3.0$^{de}$ |
| H5 (ripened pumpkin) | 10.4 ± 1.5$^a$ | 15.0 ± 1.8$^{ab}$ |
| H6 (broccoli) | 39.0 ± 2.6$^{cd}$ | 43.4 ± 2.4$^{cd}$ |
| H7 (*Phyllostachydis* Folium) | 35.2 ± 3.4$^{cd}$ | 19.5 ± 3.9$^b$ |
| H8 (Chinese wolfberry root bark) | 34.9 ± 2.5$^c$ | 49.3 ± 4.5$^d$ |
| H9 (*Angelica pubescentis*) | 39.1 ± 2.5$^{cd}$ | 16.1 ± 2.3$^{ab}$ |
| H10 (*Ramulus mori*) | 44.1 ± 3.6$^d$ | 39.9 ± 4.1$^c$ |
| H11 (*Cornus officinalis*) | 10.3 ± 1.6$^a$ | 49.8 ± 5.5$^d$ |
| H12 (*Schizandra* fruit) | 27.9 ± 2.5$^b$ | 43.7 ± 6.6$^{cd}$ |
| H13 (*Astragalus* root) | 41.1 ± 3.6$^d$ | 19.9 ± 3.1$^b$ |
| H14 (*Coix lachryma-jobi*) | 10.2 ± 1.8$^a$ | 14.8 ± 2.2$^b$ |
| H15 (*Cudrania tricuspidata*) | 9.8 ± 1.6$^a$ | 10.7 ± 1.6$^a$ |

Among 15 natural product samples, as shown in Table 1, H5 (ripened pumpkin), H14 (*Coix lachryma-jobi*), and H15 (*Cudrania tricuspidata*) showed superior inhibitory activities on ATP citrate lyase and $H_2O_2$-induced apoptosis of pancreatic islets, H2 and H11 showed superior inhibitory activity on ATP citrate lyase, and H9 showed superior inhibitory activity on $H_2O_2$-induced apoptosis of pancreatic islets.

Each of H14 and H15 showing the most excellent inhibitory activities on ATP citrate lyase and $H_2O_2$-induced apoptosis of pancreatic islets or a blended mixture with equal amounts thereof was used to measure their inhibitory activities on ATP citrate lyase and $H_2O_2$-induced apoptosis of pancreatic islets, and the results are shown in the following Table 2.

TABLE 2

| Group | ATP citrate lyase (anti-obesity) | Apoptosis of islets (anti-diabetes) |
|---|---|---|
| H14 (*Coix lachryma-jobi*) | 10.2 ± 1.8$^a$ | 14.8 ± 2.2$^b$ |
| H15 (*Cudrania tricuspidata*) | 9.8 ± 1.6$^a$ | 10.7 ± 1.6$^a$ |
| H14 + H15 | 7.8 ± 1.4$^a$ | 9.6 ± 1.3$^a$ |

As shown in Table 2, inhibitory activities on ATP citrate lyase and $H_2O_2$-induced apoptosis of pancreatic islets were remarkably increased in the blended mixture with equal amounts thereof than in each of them, leading to selection of two functional substances, *Cudrania tricuspidata* and *Coix lachryma-jobi* (H14, H15) capable of suppressing obesity and diabetes at the same time.

The results of a study in collaboration with the diabetic food company showed that 12 diabetic patients provided with the blend of H14 and H15 for 2 months showed 10% reduction in the blood glucose level, indicating that the blend of *Cudrania tricuspidata* and *Coix lachryma-jobi* has the antidiabetic effect. Further, the results of Tables 1 and 2 indicate that the blend of *Cudrania tricuspidata* and *Coix lachryma-jobi* has the anti-obesity and anti-diabetic effects.

Example 4

Purified Water Extraction of *Cudrania tricuspidata* and *Coix lachryma-jobi*

*Cudrania tricuspidata* and *Coix lachryma-jobi* were naturally dried in the shadow, and then pulverized using a pulverizer, resulting in 80-mesh sized powders. Each 20 g of *Cudrania tricuspidata* and *Coix lachryma-jobi* powders were added to 1 L of purified water which was approximately 50-fold of the weight of *Cudrania tricuspidata* and *Coix lachryma-jobi* powders, and extracted at a boiling point for 2 hours so as to obtain *Cudrania tricuspidata* and *Coix lachryma-jobi* extracts. The *Cudrania tricuspidata* and *Coix lachryma-jobi* extracts were concentrated, and vacuum freeze-drying was performed to obtain *Cudrania tricuspidata* and *Coix lachryma-jobi* powder extracts.

Example 5

Ethanol Extraction of *Cudrania tricuspidata* and *Coix lachryma-jobi*

*Cudrania tricuspidata* and *Coix lachryma-jobi* were naturally dried in the shadow, and then pulverized using a pulverizer, resulting in 80-mesh sized powders. Each 20 g of *Cudrania tricuspidata* and *Coix lachryma-jobi* powders were added to 1 L of 70% ethanol which was approximately 50-fold of the weight of *Cudrania tricuspidata* and *Coix lachryma-jobi* powders, and extracted at 80° C. for 2 hours so as to obtain *Cudrania tricuspidata* and *Coix lachryma-jobi* extracts. The *Cudrania tricuspidata* and *Coix lachryma-jobi* extracts were concentrated, and vacuum freeze-drying was performed to obtain *Cudrania tricuspidata* and *Coix lachryma-jobi* powder extracts.

The yields of purified water or 70% ethanol extracts of *Cudrania tricuspidata* and *Coix lachryma-jobi* prepared in Examples 4 and 5 were determined, and the experiment was repeated three times. The results are shown in the following Table 3.

TABLE 3

| | Yield (%) Solvent | |
|---|---|---|
| | water | 70% ethanol |
| *Coix lachryma-jobi* (Alday) | 31.71 | 2.86 |
| *Cudrania tricuspidata* | 22.41 | 21.12 |

As shown in Table 3, when *Cudrania tricuspidata* and *Coix lachryma-jobi* were extracted using purified water, the *Cudrania tricuspidata* and *Coix lachryma-jobi* powder extracts were obtained in a yield of 22.41% and 31.72%, respectively. When *Cudrania tricuspidata* and *Coix lachryma-jobi* were extracted using ethanol, the *Cudrania tricuspidata* and *Coix lachryma-jobi* powder extracts were obtained in a yield of 21.12% and 2.86%, respectively.

Example 6

Preparation of Tablet Powders of Purified Water-Extracted *Cudrania tricuspidata* and *Coix lachryma-jobi* Extracts

*Cudrania tricuspidata* and *Coix lachryma-jobi* were naturally dried in the shadow, and then pulverized using a pulverizer, resulting in 80-mesh sized powders. The *Cudrania tricuspidata* and *Coix lachryma-jobi* powders were added to purified water in a volume of approximately 50-fold of the weight of *Cudrania tricuspidata* and *Coix lachryma-jobi* powders, and extracted in the presence of microwave with a wavelength of 500±5 mm at 100° C. for 1 hour so as to obtain *Cudrania tricuspidata* and *Coix lachryma-jobi* extracts. The *Cudrania tricuspidata* and *Coix lachryma-jobi* extracts were spray-dried, and the particle size was controlled to obtain 80-mesh sized *Cudrania tricuspidata* and *Coix lachryma-jobi* powders.

Example 7

Preparation of *Cudrania tricuspidata* and *Coix lachryma-jobi* Tablet Containing *Dioscorea* Rhizome and leaf of *Morus alba* as Herbal Medicine The *Cudrania tricuspidata* and *Coix lachryma-jobi* powders obtained in Example 6 were used.

27 parts by weight of *Dioscorea* Rhizome, 9 parts by weight of the leaf of *Morus alba*, 4 parts by weight of xylitol, 3.8 parts by weight of vitamin C, 1 part by weight of octacosanol, and 0.2 part by weight of magnesium stearate, based on 100 parts by weight of *Cudrania tricuspidata* extract and *Coix lachryma-jobi* extract powders, were primarily mixed at 20° C. for 40 minutes using a Hobart mixer, and then *Cudrania tricuspidata* and *Coix lachryma-jobi* powders were added thereto, and mixed well. In this regard, all of *Dioscorea* Rhizome, the leaf of *Morus alba*, xylitol, vitamin C, octacosanol and magnesium stearate were those that were respectively pulverized using a pulverizer to have the same particle size with *Cudrania tricuspidata* and *Coix lachryma-jobi* powders.

The mixture containing the *Cudrania tricuspidata* and *Coix lachryma-jobi* powders was ripened at 20° C. for 3 hours, and tabletted using a tabletting machine at a pressure of 8 kg/cm$^2$ and an instantaneous temperature of 80° C. so as to prepare *Cudrania tricuspidata* and *Coix lachryma-jobi* tablets having a weight of 0.3 g per tablet.

The surface of the *Cudrania tricuspidata* and *Coix lachryma-jobi* tablet was spray-coated with a 3% hydroxypropyl methylcellulose (HPMC) solution so as to prepare HPMC-coated *Cudrania tricuspidata* and *Coix lachryma-jobi* tablets.

Example 8

Preparation of *Cudrania tricuspidata* and *Coix lachryma-jobi* Tablet Containing *Glycyrrhiza uralensis* and Cinnamon Bark as Herbal Medicine The *Cudrania tricuspidata* and *Coix lachryma-jobi* powders obtained in Example 6 were used.

27 parts by weight of *Glycyrrhiza uralensis*, 9 parts by weight of cinnamon bark, 4 parts by weight of xylitol, 3.8 parts by weight of vitamin C, 1 part by weight of octacosanol, and 0.2 part by weight of magnesium stearate, based on 100 parts by weight of *Cudrania tricuspidata* extract and *Coix lachryma-jobi* extract powders, were used so as to prepare *Cudrania tricuspidata* and *Coix lachryma-jobi* tablets in the same manner as in Example 7.

Example 9

Preparation of *Cudrania tricuspidata* and *Coix lachryma-jobi* Tablet Containing Golden Thread and *Astragalus* Root as Herbal Medicine The *Cudrania tricuspidata* and *Coix lachryma-jobi* powders obtained in Example 6 were used.

27 parts by weight of Golden thread, 9 parts by weight of *Astragalus* root, 4 parts by weight of xylitol, 3.8 parts by weight of vitamin C, 1 part by weight of octacosanol, and 0.2 part by weight of magnesium stearate, based on 100 parts by weight of *Cudrania tricuspidata* extract and *Coix lachryma-jobi* extract powders, were used so as to prepare *Cudrania tricuspidata* and *Coix lachryma-jobi* tablets in the same manner as in Example 7.

Example 10

Preparation of *Cudrania tricuspidata* and *Coix lachryma-jobi* Tablet Containing Atractylodes Rhizome white and *Poria* Sclerotium as Herbal Medicine The *Cudrania tricuspidata* and *Coix lachryma-jobi* powders obtained in Example 6 were used.

27 parts by weight of Atractylodes Rhizome white, 9 parts by weight of *Poria* Sclerotium, 4 parts by weight of xylitol, 3.8 parts by weight of vitamin C, 1 part by weight of octacosanol, and 0.2 part by weight of magnesium stearate, based on 100 parts by weight of *Cudrania tricuspidata* extract and *Coix lachryma-jobi* extract powders, were used so as to prepare *Cudrania tricuspidata* and *Coix lachryma-jobi* tablets in the same manner as in Example 7.

Example 11

Preparation of *Cudrania tricuspidata* and *Coix lachryma-jobi* Tablet Containing Rehmannia Root and Paeoniae Radix as Herbal Medicine The *Cudrania tricuspidata* and *Coix lachryma-jobi* powders obtained in Example 6 were used.

27 parts by weight of Rehmannia root, 9 parts by weight of Paeoniae Radix, 4 parts by weight of xylitol, 3.8 parts by weight of vitamin C, 1 part by weight of octacosanol, and 0.2 part by weight of magnesium stearate, based on 100 parts by weight of *Cudrania tricuspidata* extract and *Coix lachryma-jobi* extract powders, were used so as to prepare *Cudrania tricuspidata* and *Coix lachryma-jobi* tablets in the same manner as in Example 7.

Example 12

Preparation of *Cudrania tricuspidata* and *Coix lachryma-jobi* Tablet Containing *Dioscorea rhizome* and Leaf of *Morus alba* as Herbal Medicine and Fenugreek Seed as Secondary Functional Ingredient The *Cudrania tricuspidata* and *Coix lachryma-jobi* powders obtained in Example 6 were used.

27 parts by weight of *Dioscorea* Rhizome, 9 parts by weight of the leaf of *Morus alba,* 4 parts by weight of xylitol, 3.8 parts by weight of vitamin C, 1 part by weight of octacosanol, 0.2 part by weight of magnesium stearate, and 3 parts by weight of Fenugreek seed, based on 100 parts by weight of *Cudrania tricuspidata* extract and *Coix lachryma-jobi* extract powders, were used so as to prepare *Cudrania tricuspidata* and *Coix lachryma-jobi* tablets in the same manner as in Example 7.

Example 13

Preparation of *Cudrania tricuspidata* and *Coix lachryma-jobi* Tablet Containing *Dioscorea rhizome* and Leaf of *Morus alba* as Herbal Medicine and Ramie Leaf as Secondary Functional Ingredient The *Cudrania tricuspidata* and *Coix lachryma-jobi* powders obtained in Example 6 were used.

27 parts by weight of *Dioscorea* Rhizome, 9 parts by weight of the leaf of *Morus alba,* 4 parts by weight of xylitol, 3.8 parts by weight of vitamin C, 1 part by weight of octacosanol, 0.2 part by weight of magnesium stearate, and 2.5 parts by weight of ramie leaf, based on 100 parts by weight of *Cudrania tricuspidata* extract and *Coix lachryma-jobi* extract powders, were used so as to prepare *Cudrania tricuspidata* and *Coix lachryma-jobi* tablets in the same manner as in Example 7.

Example 14

Preparation of Tablet Powders of Ethanol-Extracted *Cudrania tricuspidata* and *Coix lachryma-jobi* Extracts

*Cudrania tricuspidata* and *Coix lachryma-jobi* were naturally dried in the shadow, and then pulverized using a pulverizer, resulting in 80-mesh sized powders. The *Cudrania tricuspidata* and *Coix lachryma-jobi* powders were added to 70% ethanol in a volume of approximately 50-fold of the weight of *Cudrania tricuspidata* and *Coix lachryma-jobi* powders, and extracted in the presence of microwave with a wavelength of 500±5 mm at 80° C. for 2 hours, and concentrated under reduced pressure so as to obtain ethanol-removed *Cudrania tricuspidata* and *Coix lachryma-jobi* extracts. The *Cudrania tricuspidata* and *Coix lachryma-jobi* extracts were spray-dried, and the particle size was controlled to obtain 80-mesh sized *Cudrania tricuspidata* and *Coix lachryma-jobi* powders.

Example 15

Preparation of *Cudrania tricuspidata* and *Coix lachryma-jobi* Tablet Containing *Dioscorea* Rhizome and Leaf of *Morus alba* as Herbal Medicine The *Cudrania tricuspidata* and *Coix lachryma-jobi* powders obtained in Example 14 were used.

27 parts by weight of *Dioscorea* Rhizome, 9 parts by weight of the leaf of *Morus alba,* 4 parts by weight of xylitol, 3.8 parts by weight of vitamin C, 1 part by weight of octacosanol, and 0.2 part by weight of magnesium stearate, based on 100 parts by weight of *Cudrania tricuspidata* extract and *Coix lachryma-jobi* extract powders, were used so as to prepare *Cudrania tricuspidata* and *Coix lachryma-jobi* tablets in the same manner as in Example 7.

Example 16

**Preparation of *Cudrania tricuspidata* and *Coix lachryma-jobi* Tablet Containing *Glycyrrhiza uralensis* and Cinnamon Bark as Herbal Medicine**

The *Cudrania tricuspidata* and *Coix lachryma-jobi* powders obtained in Example 14 were used.

27 parts by weight of *Glycyrrhiza uralensis*, 9 parts by weight of cinnamon bark, 4 parts by weight of xylitol, 3.8 parts by weight of vitamin C, 1 part by weight of octacosanol, and 0.2 part by weight of magnesium stearate, based on 100 parts by weight of *Cudrania tricuspidata* extract and *Coix lachryma-jobi* extract powders, were used so as to prepare *Cudrania tricuspidata* and *Coix lachryma-jobi* tablets in the same manner as in Example 7.

Example 17

**Preparation of *Cudrania tricuspidata* and *Coix lachryma-jobi* Tablet Containing Golden Thread and *Astragalus* Root as Herbal Medicine**

The *Cudrania tricuspidata* and *Coix lachryma-jobi* powders obtained in Example 14 were used.

27 parts by weight of Golden thread, 9 parts by weight of *Astragalus* root, 4 parts by weight of xylitol, 3.8 parts by weight of vitamin C, 1 part by weight of octacosanol, and 0.2 part by weight of magnesium stearate, based on 100 parts by weight of *Cudrania tricuspidata* extract and *Coix lachryma-jobi* extract powders, were used so as to prepare *Cudrania tricuspidata* and *Coix lachryma-jobi* tablets in the same manner as in Example 7.

Example 18

**Preparation of *Cudrania tricuspidata* and *Coix lachryma-jobi* Tablet Containing Atractylodes Rhizome White and *Poria* Sclerotium**

The *Cudrania tricuspidata* and *Coix lachryma-jobi* powders obtained in Example 14 were used.

27 parts by weight of Atractylodes Rhizome white, 9 parts by weight of *Poria* Sclerotium, 4 parts by weight of xylitol, 3.8 parts by weight of vitamin C, 1 part by weight of octacosanol, and 0.2 part by weight of magnesium stearate, based on 100 parts by weight of *Cudrania tricuspidata* extract and *Coix lachryma-jobi* extract powders, were used so as to prepare *Cudrania tricuspidata* and *Coix lachryma-jobi* tablets in the same manner as in Example 7.

Example 19

**Preparation of *Cudrania tricuspidata* and *Coix lachryma-jobi* Tablet Containing Rehmannia Root and Paeoniae Radix as Herbal Medicine**

The *Cudrania tricuspidata* and *Coix lachryma-jobi* powders obtained in Example 14 were used.

27 parts by weight of Rehmannia root, 9 parts by weight of Paeoniae Radix, 4 parts by weight of xylitol, 3.8 parts by weight of vitamin C, 1 part by weight of octacosanol, and 0.2 part by weight of magnesium stearate, based on 100 parts by weight of *Cudrania tricuspidata* extract and *Coix lachryma-jobi* extract powders, were used so as to prepare *Cudrania tricuspidata* and *Coix lachryma-jobi* tablets in the same manner as in Example 7.

Experimental Example 1

Sensory Evaluation

Sensory evaluation including taste, flavor, color, appearance, chewness, and preference was performed with respect to the *Cudrania tricuspidata* and *Coix lachryma-jobi* tablets prepared in Examples 7 to 11 in accordance with a 9-point hedonic scale, and the results are shown in the following Table 4. The sensory evaluation was performed by 20 participants (each 10 of male and female participants) who have been engaged in food-related fields for 3 years or longer and experienced in sensory evaluation. The results are shown in the following Table 4.

TABLE 4

| Group | Taste | Flavor | Color | Appearance | Texture | Preference |
|---|---|---|---|---|---|---|
| Example 7 | 7.7 | 7.6 | 7.7 | 7.9 | 7.7 | 7.7 |
| Example 8 | 8.3 | 8.5 | 8.6 | 8.4 | 8.7 | 8.5 |
| Example 9 | 8.2 | 8.3 | 8.2 | 8.2 | 7.8 | 8.1 |
| Example 10 | 8.3 | 8.5 | 8.4 | 8.5 | 8.5 | 8.3 |
| Example 11 | 8.2 | 8.4 | 8.1 | 8.0 | 8.3 | 8.3 |

The marks in the sensory test items of Table 4 are average values (rounded off to two decimal places) obtained by dividing the total scores by the number of panel members, and higher score value in the sensory test items represents more excellent sensory properties.

As shown in Table 4, the *Cudrania tricuspidata* and *Coix lachryma-jobi* tablets prepared in Examples 7 to 11 presented 7 points or higher in taste, flavor, color, appearance, texture, and preference, indicating excellent sensory properties.

Experimental Example 2

**Measurement of Blood Sugar-Lowering Effect of *Cudrania tricuspidata* and *Coix lachryma-jobi* Extracts**

Oral glucose tolerance test was performed with respect the *Cudrania tricuspidata* and *Coix lachryma-jobi* extracts prepared in Examples 4 and 5. The results are shown in the following Table 5.

TABLE 5

| | Blood sugar level (min, mg/dL) | | | | | |
|---|---|---|---|---|---|---|
| Sample | 0 | 30 | 60 | 90 | 120 | Blood sugar increase[1] |
| *Coix lachryma-jobi* (water) | 127.9 ± 19.2 | 349.8 ± 33.9 | 295.1 ± 46.1 | 197.1 ± 51.7 | 161.4 ± 48.8 | 33.5 ± 37.2 (26) |
| *Coix lachryma-jobi* (ethanol)[3] | — | — | — | — | — | |

TABLE 5-continued

| | Blood sugar level (min, mg/dL) | | | | | Blood sugar increase[1] |
|---|---|---|---|---|---|---|
| Sample | 0 | 30 | 60 | 90 | 120 | |
| Cudrania tricuspidata (water) | 120.8 ± 25.8 | 279.3 ± 45.8 | 237.4 ± 44.6 | 167.0 ± 32.1 | 151.1 ± 31.9 | 30.3 ± 27.4 (25) |
| Cudrania tricuspidata (ethanol) | 121.4 ± 11.3 | 276.1 ± 43.7 | 221.7 ± 56.2 | 170.5 ± 47.2 | 148.8 ± 35.7 | 27.4 ± 35.3 (23) |
| Glucose | 116.6 ± 20.9 | 267.7 ± 45.3 | 242.4 ± 47.2 | 187.7 ± 32.3 | 162.0 ± 29.1 | 45.4 ± 24.6 (39) |

Note)
animal: ICR mouse (ave. body wt., 28 g)
Administration dose of glucose: 2 g/kg bw
Administration dose of sample: 500 mg/kg bw
[1],[2]glycemic index (mg/dL) after 120 min (0 min vs 120 min), as percentage (%)
[3]data is insufficient and thus not shown,
[ns] not significant As shown in Table 5, the *Cudrania tricuspidata* and *Coix lachryma-jobi* extracts showed lower glycemic index than the control group, glucose, indicating that the *Cudrania tricuspidata* and *Coix lachryma-jobi* extracts have excellent blood glucose-lowering effects.

Experimental Example 3

Measurement of Anti-Obesity Effect of *Cudrania tricuspidata* and *Coix lachryma-jobi* Extracts In order to measure anti-obesity effect of the *Cudrania tricuspidata* and *Coix lachryma-jobi* extracts prepared in Examples 4 and 5, their effects on lipid accumulation upon differentiation of a preadipocyte cell 3T3-L1 into adipocyte were tested. The specific method is as follows.

3-1: Culture of 3T3-L1 Preadipocyte Cell

The preadipocyte cells were cultured in DMEM (Dulbecco's modified Eagle's medium) supplemented with 1% P/S (penicillin-streptomycin) and 10% BCS (bovine calf serum) at 37° C. and 5% $CO_2$. The cells were cultured at 3 day-intervals. When the cells reached 70% confluence in a 100Φ plate, they were washed with PBS (phosphate buffered saline), and then left in a 0.25% trypsin-EDTA solution at 37° C. and 5% $CO_2$ for 3 minutes. The detached cells were maintained by subculturing.

3-2: Induction of 3T3-L1 Preadipocyte Cell Differentiation

In order to induce differentiation of preadipocyte cells, cells were seeded in DMEM supplemented with 10% BCS and 1% P/S in a 6-Well plate at a density of $1.25 \times 10^5$ cells/well. After 2 days, the medium was replaced, and cells were completely fused at 3~4 days. Differentiation of the fused cells was induced in a differentiation medium MDI (IBMX, Dexa, Insulin). At this time, in order to examine the effect of *Cudrania tricuspidata* and *Coix lachryma-jobi* extracts on adipocyte differentiation, the extract sample was added to the differentiation medium at a concentration of 1 mg/ml. At 2 days after differentiation induction, the medium was replaced with DMEM containing the sample, 10% FBS, 1% P/S, and 5 μg/ml insulin. From 4 days after differentiation induction, the medium was replaced with DMEM containing 10% FBS and 1% P/S once every 2 days to induce differentiation.

3-3: Oil-Red O Staining

Oil-red O staining and quantification were performed using cells at 7~9 days of differentiation. After removing 10% FBS DMEM, cells were washed with PBS twice, and fixed in 10% formalin at 4° C. for 1 hour, and then washed with distilled water three times. The washed cells were stained for 1 hour with an oil-red O solution specific to lipid droplets produced in cells. After staining, the staining solution was removed, and the cells were washed with distilled water three times. Then, each well was filled with distilled water, and examined under a microscope. For quantification of neutral lipids, distilled water was removed from the well, and 2 ml of 100% iso-propyl alcohol was added to the completely dried well to elute oil-red O. Absorbance was measured at 490 nm using an ELISA reader.

In order to examine the effect of each sample on lipid accumulation during differentiation of 3T3-L1 adipocytes, each sample was diluted with the differentiation medium at a concentration of 1 mg/ml to perform Oil-red O staining. As compared to the control, the *Coix lachryma-jobi* ethanol extract showed 92.9% lipid accumulation, the *Cudrania tricuspidata* water extract showed 60.9% lipid accumulation, and the *Cudrania tricuspidata* ethanol extract showed the lowest 20.5% lipid accumulation (Table 6).

These results support that *Coix lachryma-jobi* and *Cudrania tricuspidata* extracts suppress adipocyte differentiation directly involved in obesity, indicating that *Coix lachryma-jobi* and *Cudrania tricuspidata* extracts have anti-obesity effect.

TABLE 6

| Sample | Lipid accumulation (%) |
|---|---|
| *Cudrania tricuspidata* water extract | 60.9 |
| *Cudrania tricuspidata* ethanol extract | 20.5 |
| *Coix lachryma-jobi* water extract | 88.7 |
| *Coix lachryma-jobi* ethanol extract | 92.9 |

* Concentration: 1 mg/ml

Preparation Example 1

Preparation of *Cudrania tricuspidata* and *Coix lachryma-jobi* Tablet Product

Based on 1 kg of raw materials, 40% (400 g) of *Cudrania tricuspidata* powder extract, 40% (400 g) of *Coix lachryma-jobi* powder extract, 12% (120 g) of dextrin, and 5% (50 g) of vitamin C were mixed, and then 3% (20 g) of HPMC was blended thereto so as to prepare a *Cudrania tricuspidata* and *Coix lachryma-jobi* tablet product (Table 7).

TABLE 7

| Raw materials | Ratio % (g) |
| --- | --- |
| *Cudrania tricuspidata* powder extract | 40 (400) |
| *Coix lachryma-jobi* powder extract | 40 (400) |
| Dextrin | 12 (120) |
| Vitamin C | 5 (50) |
| HPMC | 3 (30) |
| Total | 10 (1000) |

ADVANTAGEOUS EFFECTS

Since the *Cudrania tricuspidata* and *Coix lachryma-jobi* tablet of the present invention comprises herbal medicines, the *Cudrania tricuspidata* and *Coix lachryma-jobi* tablet having improved functions by herbal medicines and a preparation method thereof are provided. The *Cudrania tricuspidata* and *Coix lachryma-jobi* tablet further comprising functional substances and a preparation method thereof are also provided. Further, the *Cudrania tricuspidata* and *Coix lachryma-jobi* extracts of the present invention exhibit excellent inhibitory effects on ATP citrate lyase and $H_2O_2$-included apoptosis of pancreatic islets, and excellent anti-obesity and blood sugar-lowering effects, and thus can be used as a pharmaceutical composition or functional food for the prevention or treatment of obesity and diabetes. Furthermore, the *Cudrania tricuspidata* and *Coix lachryma-jobi* tablet of the present invention is easy to carry, and store *Cudrania tricuspidata* and *Coix lachryma-jobi*, and intake *Cudrania tricuspidata* and *Coix lachryma-jobi*, because *Cudrania tricuspidata* and *Coix lachryma-jobi* are processed in a form of tablet.

What is claimed is:

1. A method for preparing a tablet for suppressing obesity or lowering blood sugar in a mammal, consisting essentially of the steps of:
   (a) mixing *Cudrania tricuspidata* extract and *Coix lachryma-jobi* extract with a therapeutically effective amount of one or more herbal medicines selected from the group consisting of red ginseng, ginseng, *Dioscorea* Rhizome, the leaf of *Morus alba*, the fruit, stem, and leaf of *Hovenia dulcis*, *Glycyrrhiza uralensis*, cinnamon bark, Golden thread, *Rubus coreanus* Miquel, Dodder seed, *Cnidium* fruit, *Lycium* fruit, *Schizandra* fruit and *Astragalus* root to prepare a first mixture;
   (b) adding to the first mixture one or more functional ingredients selected from the group consisting of vitamin, saccharide, squalene, taurine, octacosanol and sodium alginate, and mixing them so as to prepare a second mixture;
   (c) ripening the second mixture at 5-20° C. for 10-20 hours;
   (d) preparing tablets using the second mixture and a tabletting machine; and
   (e) coating the tablets with a hydroxypropyl methylcellulose solution to yield the tablet for suppressing obesity or lowering blood sugar in a mammal.

2. A method for suppressing obesity or lowering blood sugar in a mammal, consisting essentially of the step of administering to said mammal the tablet prepared according to the method of claim 1.

3. The method of claim 1, wherein the *Cudrania tricuspidata* extract is extracted using a solvent of 70% ethanol; the *Coix lachryma-jobi* extract is extracted using a solvent of water; and the *Cudrania tricuspidata* extract and the *Coix lachryma-jobi* extract are mixed at a weight ratio of 1:1.

4. The method of claim 1, wherein
   step (a) consists essentially of mixing *Cudrania tricuspidata* extract and *Coix lachryma-jobi* extract with 10-50 parts by weight of one or more herbal medicines selected from the group consisting of red ginseng, ginseng, *Dioscorea* Rhizome, the leaf of *Morus alba*, the fruit, stem, and leaf of *Hovenia dulcis*, *Glycyrrhiza uralensis*, cinnamon bark, Golden thread, *Rubus coreanus* Miquel, Dodder seed, *Cnidium* fruit, *Lycium* fruit, *Schizandra* fruit and *Astragalus* root, based on 100 parts by weight of *Cudrania tricuspidata* extract and *Coix lachryma-jobi* extract so as to prepare a first mixture; and
   step (b) consists essentially of adding to the first mixture one or more functional ingredients selected from the group consisting of 1-5 parts by weight of vitamin, 1-10 parts by weight of saccharide, 0.5-5 parts by weight of squalene, 0.5-5 parts by weight of taurine, 0.1-5 parts by weight of octacosanol and 1-5 parts by weight of sodium alginate, based on 100 parts by weight of *Cudrania tricuspidata* extract and *Coix lachryma-jobi* extract, and mixing them so as to prepare a second mixture.

* * * * *